(12) United States Patent
Alvelind

(10) Patent No.: US 8,486,503 B2
(45) Date of Patent: Jul. 16, 2013

(54) SURGICAL TAPE

(75) Inventor: Lars Alvelind, Molnlycke (SE)

(73) Assignee: Molnlycke Health Care AB (SE)

(*) Notice: Subject to any disclaimer, the term of this patent is extended or adjusted under 35 U.S.C. 154(b) by 293 days.

(21) Appl. No.: 12/745,032

(22) PCT Filed: Dec. 4, 2008

(86) PCT No.: PCT/SE2008/051407
§ 371 (c)(1),
(2), (4) Date: Jul. 21, 2010

(87) PCT Pub. No.: WO2009/078787
PCT Pub. Date: Jun. 25, 2009

(65) Prior Publication Data
US 2010/0304072 A1   Dec. 2, 2010

(30) Foreign Application Priority Data
Dec. 17, 2007   (SE) ...................................... 0702803

(51) Int. Cl.
*B32B 9/00*   (2006.01)
*B32B 5/02*   (2006.01)
*B32B 5/08*   (2006.01)
*B32B 7/12*   (2006.01)

(52) U.S. Cl.
USPC ............ 428/40.1; 428/98; 428/119; 428/343; 428/351

(58) Field of Classification Search
USPC ............................ 428/40.1, 343, 98, 119, 351
See application file for complete search history.

(56) References Cited

U.S. PATENT DOCUMENTS

| | | | |
|---|---|---|---|
| 3,121,021 A | 2/1964 | Copeland | |
| 3,853,598 A | 12/1974 | Raguse | |
| 3,908,650 A | 9/1975 | Dunshee et al. | |
| 4,292,360 A | 9/1981 | Riedel et al. | |
| 4,303,724 A | 12/1981 | Sergeant et al. | |
| 5,246,773 A | 9/1993 | Mamish | |
| 5,496,603 A | 3/1996 | Riedel et al. | |
| 6,048,806 A | 4/2000 | Deeb et al. | |

FOREIGN PATENT DOCUMENTS

| | | |
|---|---|---|
| AU | 2008339084 | 12/2008 |
| CA | 2707617 | 6/2010 |
| CN | 101896146 | 12/2008 |
| EP | 2231087 | 9/2010 |
| GB | 2 195 673 A | 4/1988 |
| JP | H05-070749 | 9/1991 |
| JP | H07-088130 | 9/1993 |
| JP | 2000-117917 | 4/2000 |
| JP | 2004-229830 | 8/2004 |
| JP | 2011-506037 | 6/2010 |
| KR | 10-2010-0106972 | 10/2010 |

(Continued)

OTHER PUBLICATIONS

International Search Report, dated Jun. 24, 2009, from corresponding PCT application.
International Preliminary Report on Patentability and Written Opinion issued on Jun. 22, 2010 for WO/2009/078787 (PCT/SE2008/051407) (6 pages).

(Continued)

*Primary Examiner* — Patricia Nordmeyer
(74) *Attorney, Agent, or Firm* — Ballard Spahr LLP

(57) ABSTRACT

A surgical tape (1) includes a carrier (2, 3), on one side coated with an adhesive (4) and including a layer of non-woven (3). A layer of plastic film (2) is laminated to the layer of non-woven and the surgical tape (1) is tearable in a cross direction relative its longitudinal direction and liquid impermeable.

10 Claims, 1 Drawing Sheet

FOREIGN PATENT DOCUMENTS

| | | |
|---|---|---|
| SE | 0702803-8 | 12/2007 |
| WO | 93/15245 A1 | 8/1993 |
| WO | 00/20201 A1 | 4/2000 |
| WO | WO/2009/078787 | 6/2009 |

OTHER PUBLICATIONS

Supplementary European Search Report issued on Nov. 21, 2012 for European Patent Application No. 20080861506, which was filed on Dec. 4, 2008 [Inventor—Alvelind; Applicant—Mölnlycke Health Care AB] [3 pages].

SURGICAL TAPE

TECHNICAL FIELD

The present invention relates to a surgical tape including a carrier, which on one side is coated with an adhesive and which includes a layer of nonwoven.

BACKGROUND OF THE INVENTION

A surgical tape (OP-tape) consisting of a non-woven coated with an adhesive on one side is known. Such a tape has several very good properties, such as a good stretchability in the longitudinal direction and air permeability, which result in that it can be applied on skin without being experienced as uncomfortable or disturbing. It is furthermore manually tearable, which makes it easy to remove tape strips of a desired length from a roll of such tape. It is however not liquid impermeable and can therefore not be used during conditions where liquid impermeability is a requirement. Under such conditions one is obliged to use OP-tapes consisting of a plastic layer coated with adhesive. Such tapes are however not tearable.

In this description and in the patent claims the term "tearable" means that a tape by manual tearing can be separated in two parts, the tear line being essentially straight and extended in a cross direction of the tape. Furthermore, the tearing shall be accomplished without any noticeable elongation deformation of the tape in the end areas turned against each other of the two parts of the tape resulting from a tearing.

The objective of the invention is firstly to provide a OP-tape which is tearable and liquid impermeable. Secondly a OP-tape according to the invention should also have good bendability and good stretchability.

SUMMARY OF THE INVENTION

These objectives are accomplished by a surgical tape including a carrier which on one side is coated with adhesive and which includes a layer of non-woven and a layer of plastic film laminated to the layer of non-woven, characterized in that the length direction of the surgical tape is perpendicular to the machine direction of the nonwoven layer, the basis weight of the non-woven layer is 20-100 g/m² and the plastic film has a thickness between 10-50 micrometer, wherein the surgical tape is tearable in a cross direction relative to its longitudinal direction and liquid impermeable.

In a preferred embodiment the adhesive coating is applied on one side of the non-woven layer and the plastic film is applied on the opposite side of the non-woven layer. The force required to tear the surgical tape in its cross direction is preferably 1.5-15 N, preferably 3-5 N.

The stretchability of the surgical tape after removing of the release layer is advantageously between 50-250%, preferably between 100-175%. The bendability, i.e. the bending length, is preferably less than 5 cm for the laminate of plastic film and non-woven included in the tape.

The basis weight of the non-woven layer should preferably be 30-50 g/m². Before use a release layer (5; 10) covering the adhesive coating (4; 9) is included in the surgical tape, said release layer being manufactured of a tearable material.

BRIEF DESCRIPTION OF THE DRAWINGS

The invention shall now be described with reference to the enclosed figures, of which.

DESCRIPTION OF EMBODIMENTS

Figure 1:
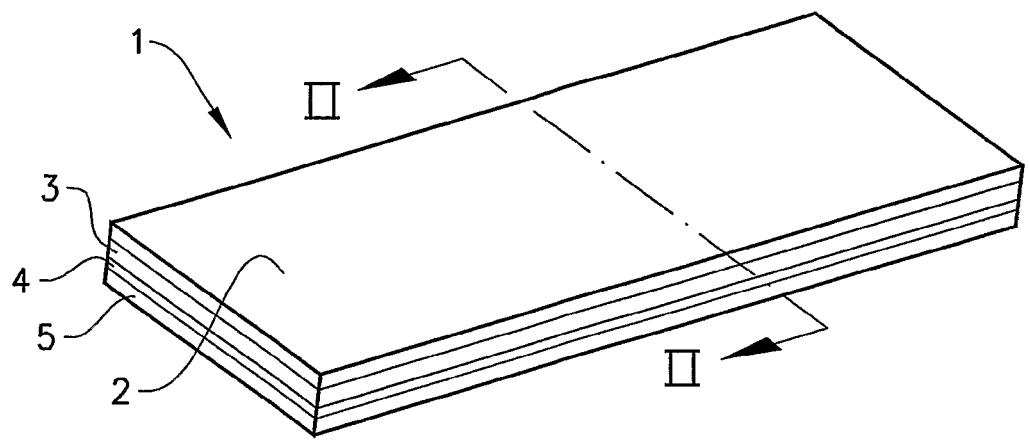
FIG. 1 schematically shows a perspective view from above of a piece of an OP-tape according to a first preferred embodiment of the invention.
Figure 2:
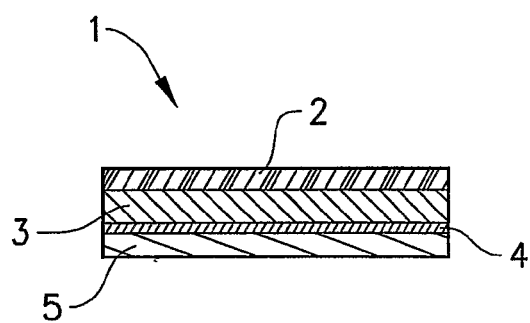
FIG. 2 shows a sectional view along line II-II in FIG. 1.

The piece 1 of OP-tape shown in FIGS. 1 and 2 has a carrier coated with an adhesive coating 4. The carrier consists of a laminate of a layer 2 of plastic film and a layer 3 of non-woven. A so called release layer 5 is furthermore easily releaseably attached to the adhesive coating to protect the adhesive coating against dirt and other impurities before use and for preventing the tape from being unintentionally attached to an object before use.

The plastic film in the layer 2 consists suitably of polyethylene plastic but also other plastics, such as polyurethane, polyester and polypropene can be used.

A non-woven material has greater strength but less stretchability in the machine direction, that is the running direction of the web onto which the fibers are laid at manufacture of the material, than in the cross direction, that is a direction perpendicular to the machine direction. In a OP-tape according to the invention the longitudinal direction of the OP-tape extends perpendicular to the machine direction of the non-woven material. Thereby is accomplished that the OP-tape obtains a good stretchability in its longitudinal direction and is tearable in its cross direction, which coincidences with the machine direction of the non-woven material. By the longitudinal direction of the OP-material is meant the direction, in which the tape can be uncoiled from the roll of tape. The longitudinal direction of a teared sheet of tape is thus always perpendicular against the machine direction of the non-woven material independent of if the length of the tear peace is larger than the width of the tape or not.

The non-woven material consists suitably of a non-woven manufactured by dry laid carding technology. Non-woven materials manufactured in other ways, e.g. wetlaid or spunlaid non-woven, are also suitable to use. The fibers in the non-woven material can be chemically bonded, bonded with the aid of heat or mechanically bonded. The fibers included in the non-woven material can be cellulose based fibers, e.g. viscose fibers, polymer based fibers, e.g. polyester fibers or polypropylene fibers, or mixtures thereof. The fibers can consist of staple fibers or continuous fibers and mixtures thereof. Suitable basis weight of the non-woven layer is dependent of the included fiber types, the fiber mixture and the manufacturing process.

The adhesive coating 4 consists of a pressure sensitive adhesive (PSA), e.g. a hot melt adhesive. Other types of PSA-adhesive can also be used, e.g. acrylate adhesive or silicone adhesive.

Figure 4:
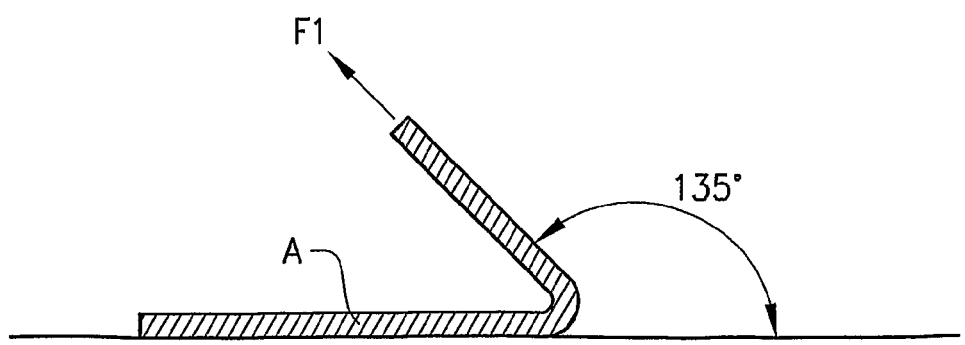
FIG. 4 illustrates a method of measuring adhesive force against skin.

Since the properties of the skin varies from person to person, also the adhesive capacity against skin of the adhesive coating certainly varies for different patients. The adhesive force is also dependent on the mechanical properties of the carrier layer. The standard methods for measuring adhesive force existing today use plates of different kinds, e.g. of steel or glass, and does not give values relevant for measuring adhesive force against skin. The values of adhesive forces against skin of an adhesive given henceforth should be measured with a method, which is schematically illustrated in FIG. 4 and which has been developed by the applicant.

Strips of an OP-tape, of which the adhesive force against skin shall be measured, is punched to a size of 25×125 mm. Thereafter the strips are placed on the skin of the back of six healthy volunteers. The strips are carefully applied with a finger. Finally the strips are pressed firmly against the skin during 3 seconds with the aid of a sponge of foamed plastic (42×182 mm, thickness=48 mm) glued to a steel plate (50× 200 mm, thickness=1 mm). The press force is estimated to 6 kN/m². The strips are left on the skin during 4 hours. The strips are then drawn off with a rate of 25 mm/second and the pull force F1 is measured. The angle of pull, that is the obtuse angle formed between the skin surface and the pulled off part of the strip, shall be 135°. The adhesive force against skin of the strip is constituted by the mean force of force F1.

The adhesive force against skin of the adhesive shall be between 1.5-15 N, preferably between 1-3 N measured according to this method.

The release layer 5 should be constituted of a tearable material and can suitably consist of release paper, that is a paper coated with a thin layer of silicone.

The plastic layer 2 and the non-woven layer 3 are preferably laminated to each other by a water based glue, e.g. a acrylate glue, or by a hot melt adhesive. The glue is preferably applied in a pattern, e.g. with the aid of an engraving roller, but could also be applied in a continuous layer or applied with the aid of a spray nozzle.

The plastic layer 2 should not be so thick that it to any appreciable extent makes the tearing of the OP-tape more difficult. The plastic layer has a larger stretchability than the non-woven material and if it is too thick it would not rupture at the same time as the non-woven material, which will lead to an unsuitable distribution of the tearing force. The plastic layer 2 should neither be too thin but must be able to follow the stretching of the non-woven material without locally rupturing, thereby jeopardizing the liquid impermeability of the OP-tape. A suitable thickness depends except from the chosen plastic material also on the properties of the chosen non-woven and the glue used for laminating.

The liquid impermeability of the OP-tape should be larger than 900 mm and preferably larger than 000 mm water head, in order for the tape to be regarded as liquid impermeable.

In addition to be stretchable the OP-tape should have certain bendability to function well, e.g. to also be able to follow uneven body contours. The bendability, i.e. the bending length, of the OP-tape should therefore suitable be less than 5 cm measured with removed release layer and adhesive layer.

In order for the OP-tape to be regarded as manually tearable the force required for tearing the OP-tape in its cross direction should be between than 1.5-15 N, preferably 3-5 N, with the release layer remaining on the OP-tape.

Figure 3:
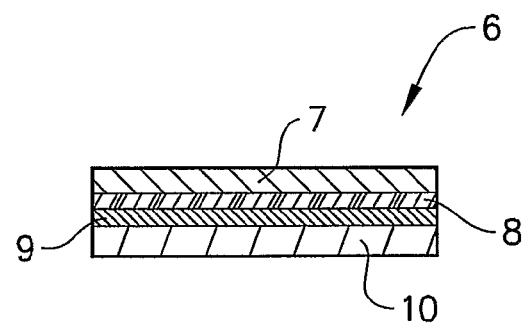
FIG. 3 shows a similar view as FIG. 2 of an OP-tape according to a second preferred embodiment of the invention.

In FIG. 3, an OP-tape 6 according to a second embodiment of the invention is shown in a view similar to FIG. 2. This tape differs from the embodiment described with reference to FIGS. 1 and 2 by the non-woven layer 7 being placed outermost and the adhesive coating 9 being applied on the lower side of the plastic film 8. Also in this embodiment a release layer 10 protects the adhesive coating 9. The components in the OP-tape 6 are apart from above mentioned differences in localization similar to corresponding components in the OP-tape according to FIGS. 1 and 2.

The embodiment shown in FIG. 3 is less preferred than the embodiment in FIGS. 1 and 2 due to the fact that the risk for delamination of the OP-tape when pulled off metal surfaces, e.g. an anesthesia bow, is larger than in the first embodiment.

EXAMPLE

A sample of a first tape (sample 1) was tested for stretchability and tearability. The tape consisted of a spunlace non-woven layer of polyester with a basis weight of 40 g/m² "PSP40 V684" from PGI Nonwovens, France, laminated with a laminating glue "Sanicare W7005A" from Henkel KGaA, Germany, to a plastic film of polyethylen with a thickness of 27.5 µm from Mayaflex 381, RKW ACE S.A., Belgium. The laminate was in turn coated with a hot melt "Synthetic rubber based Hot melt, 30 gsm Duro-Tak 8673E" from National Starch & Chemical AB, USA, which was protected by a release layer of siliconized bleached paper with a basis weight 90 g/m² "Releasepaper PMC90" from Loparex OY. For the tests concerning tearability the release layer was left on the product but the stretchability tests was performed on the material after removing of the release layer, in order to reflect real use of the material.

A sample of a second tape (sample 2) was tested for water permeability and bendability. This tape was similar to the first tape apart from lacking hot melt layer and release layer. The hot melt layer is supposed to influence the bendability but it is difficult to test because the risk is large that adhesive residues sticks to the measuring equipment.

A known OP-tape of mark "Klinidrape" from Mölnlycke Health Care AB, Sweden, was tested as a reference for stretchability and tearability (sample 3). Material composition of sample 3: so called chemical bond fabric of polyester, 52 g/m² "PNR 50V684" from PGI Nonwovens, France, provided with an adhesive layer of EVA (Etylen Vinyl Acetat) based hot melt 45 g/m² "DT139" from National Starch & Chemical AB and a release layer of siliconized bleached paper with a basis weight of 90 g/m² "Releasepaper PMC90" from Loparex Oy. For the tests concerning tearability the release layer was left on the product but the stretchability tests were conducted on the material after removal of the release layer in order to reflect real use of the material.

Measuring Methods

Stretchability was measured according to T-229 rev. 9" "Nonwoven Tensile strength" (annex 1).

Tearability was measured according to T-231 rev. 5 "Tear strength Elmendorf" (annex 2).

The liquid impermeability was measured according to T-280 rev. 7 "Water permeability according to SS-EN" (annex 3).

The bendability was measured according to T-307 rev. 2 (annex 4).

Annexes 1-4 are included as annexes in the present application.

The tests gave the following results.

The stretchability, the elongation at break, of the first tape was 153.7% in dry condition and 151.0% in wet condition, that is after the sample during a certain time had been drowned in liquid.

The stretchability of the reference tape was 210.6% in dry condition and 223.1% in wet condition.

The stretchability was of course measured with the release layer removed.

The tearability of the first tape was 3.3 N and for the reference tape 3.5 N. I should be noted that the release layer was left on the samples when the tearability test was performed.

The water impermeability showed that the second tape did not let water through at a water head of 1000 mm.

The bendability, i.e. the bending length, of the second tape was 3.8 cm in the machine direction and 2.9 cm in the cross direction.

As is evident from the performed tests an OP-tape according to the embodiment described in the example is tearable to the same extent as the known tearable OP-tape with only non-woven as carrier material. Furthermore is it liquid impermeable up to more than 1000 mm water head, a value clearly exceeding the value needed for the area of use for such a tape. Also stretchability and bendability are clearly within the requirements that can be made on a OP-tape.

The shown embodiments can of course be varied within the scope of the invention. For example can laminating of non-woven and plastic film be made in other ways than through gluing, e.g. by spot-welding with the aid of ultra sound or heat. The release layer can be in two parts, one part can be slightly overlapping the other part so that a grip tap is formed, or be wider than the tape itself. The adhesive coating can be discontinues, e.g. applied by spraying, or continuous. The scope of the invention shall therefore only be limited of the content of the enclosed claims.

The invention claimed is:

1. Surgical tape comprising a carrier, which on one side is coated with adhesive, and which comprises a non-woven layer and a layer of plastic film laminated to the non-woven layer, wherein the length direction of the surgical tape is perpendicular to the machine direction of the non-woven layer, wherein the basis weight of the non-woven layer is 20-100 $g/m^2$, wherein the plastic film has a thickness between 10-50 micrometer, and wherein the surgical tape is tearable in a cross direction relative to its longitudinal direction and is liquid impermeable.

2. Surgical tape according to claim 1, wherein the adhesive coating is applied on one side of the non-woven layer and the plastic film is applied on the opposite side of the non-woven layer.

3. Surgical tape according to claim 2, wherein the force required for tearing the surgical tape in its cross direction is between 1.5-15 N.

4. Surgical tape according to claim 2, wherein the force required for tearing the surgical tape in its cross direction is between 3-5 N.

5. Surgical tape according to claim 1, wherein the force required for tearing the surgical tape in its cross direction is between 1.5-15 N.

6. Surgical tape according to claim 5, wherein the stretchability of the surgical tape is between 50-250% in the longitudinal direction.

7. Surgical tape according to claim 1, wherein the bendability is less than 5 cm for the laminate of plastic film and non-woven layer included in the tape.

8. Surgical tape according to claim 1, wherein the basis weight of the non-woven layer is 30-50 $g/m^2$.

9. Surgical tape according to claim 1, comprising, before use, a release layer covering the adhesive coating, said release layer being manufactured of a tearable material.

10. Surgical tape according to claim 1, wherein the force required for tearing the surgical tape in its cross direction is between 3-5 N.

* * * * *

UNITED STATES PATENT AND TRADEMARK OFFICE
CERTIFICATE OF CORRECTION

PATENT NO. : 8,486,503 B2 Page 1 of 1
APPLICATION NO. : 12/745032
DATED : July 16, 2013
INVENTOR(S) : Lars Alvelind It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 328 days.

Signed and Sealed this
Eighth Day of September, 2015

Michelle K. Lee
*Director of the United States Patent and Trademark Office*